US008053586B2

(12) United States Patent
Osborne et al.

(10) Patent No.: US 8,053,586 B2
(45) Date of Patent: Nov. 8, 2011

(54) ALKYLENE OXIDE RECOVERY SYSTEMS

(75) Inventors: Bernie B. Osborne, Hurricane, WV (US); Fred A. Conneway, Titusville, FL (US); Clarence P. Stadlwieser, Sherwood Park (CA); Harvey E. Andresen, Luling, LA (US)

(73) Assignee: Dow Technology Investments LLC, Midland, MI (US)

( * ) Notice: Subject to any disclaimer, the term of this patent is extended or adjusted under 35 U.S.C. 154(b) by 257 days.

(21) Appl. No.: 12/460,775

(22) Filed: Jul. 24, 2009

(65) Prior Publication Data
US 2010/0063306 A1 Mar. 11, 2010

Related U.S. Application Data

(60) Provisional application No. 61/137,493, filed on Jul. 31, 2008, provisional application No. 61/137,494, filed on Jul. 31, 2008, provisional application No. 61/137,517, filed on Jul. 31, 2008, provisional application No. 61/137,514, filed on Jul. 31, 2008, provisional application No. 61/137,485, filed on Jul. 31, 2008.

(51) Int. Cl.
C07D 301/32 (2006.01)
B01D 3/38 (2006.01)
B01D 3/34 (2006.01)

(52) U.S. Cl. ............. 549/541; 549/538; 203/76; 203/81; 203/83; 203/85; 203/95

(58) Field of Classification Search .................. 549/538, 549/541; 203/76, 81, 83, 85, 95
See application file for complete search history.

(56) References Cited

U.S. PATENT DOCUMENTS

| | | |
|---|---|---|
| 2,615,901 A | 10/1952 | McClellan |
| 2,697,104 A | 12/1954 | Lowe et al. |
| 2,771,473 A | 11/1956 | Courter |
| 2,775,600 A | 12/1956 | Maslan |
| 2,815,650 A | 12/1957 | McIntire et al. |
| 3,094,401 A | 6/1963 | Lidell |
| 3,165,539 A | 1/1965 | Lutz |
| 3,174,262 A | 3/1965 | Lutz |
| 3,216,177 A | 11/1965 | Bracken et al. |
| 3,398,062 A | 8/1968 | Tsao |
| 3,418,338 A | 12/1968 | Gilman et al. |
| 3,531,376 A | 9/1970 | Minoda et al. |
| 3,729,899 A | 5/1973 | Cunningham |
| 3,745,092 A | 7/1973 | Vanderwater |
| 3,766,714 A | 10/1973 | Cunningham et al. |
| 3,867,113 A | 2/1975 | Foster et al. |
| 3,904,656 A | 9/1975 | Broz |
| 3,948,621 A | 4/1976 | Cocuzza et al. |
| 3,964,980 A | 6/1976 | Ozero |
| 4,033,617 A | 7/1977 | Cocuzza et al. |
| 4,134,797 A | 1/1979 | Ozero |
| 4,597,833 A | 7/1986 | N'eel et al. |
| 4,845,296 A | 7/1989 | Ahmed et al. |
| 4,966,657 A | 10/1990 | Delannoy et al. |
| 4,983,260 A | 1/1991 | N'eel et al. |
| 5,233,060 A | 8/1993 | Pendergast et al. |
| 5,529,667 A | 6/1996 | Coffey |
| 6,080,897 A | 6/2000 | Kawabe |
| 6,123,812 A | 9/2000 | Bessling et al. |
| 6,437,199 B1 | 8/2002 | Oka et al. |
| 6,498,272 B1 | 12/2002 | Schröder et al. |
| 6,833,057 B1 | 12/2004 | Bessling et al. |
| 7,179,875 B2 | 2/2007 | Fuchs et al. |
| 2004/0236049 A1 | 11/2004 | Fuchs et al. |
| 2005/0103617 A1 | 5/2005 | Andreis et al. |
| 2005/0277778 A1 | 12/2005 | Viswanathan et al. |
| 2006/0264648 A1 | 11/2006 | Beekman et al. |

FOREIGN PATENT DOCUMENTS

| | | |
|---|---|---|
| CA | 978197 A1 | 11/1975 |
| CZ | 104663 | 8/1962 |
| DE | 1165567 | 3/1964 |
| DE | 199 24 533 | 11/2000 |
| DE | 19924533 | 11/2000 |
| DE | 101 38 150 | 2/2003 |
| DE | 10138150 | 2/2003 |
| EP | 0 181 273 | 5/1986 |
| EP | 0181273 | 5/1986 |
| FR | 1 330 900 | 5/1963 |
| FR | 1330900 | 5/1963 |
| FR | 2 851 564 | 8/2004 |
| FR | 2851564 | 8/2004 |
| GB | 564646 | 10/1944 |

(Continued)

OTHER PUBLICATIONS

International Search Report and Written Opinion from related PCT Application PCT/US 2009/004321, dated Nov. 5, 2009 (11 pgs).

(Continued)

Primary Examiner — Bernard Dentz
(74) Attorney, Agent, or Firm — Brooks, Cameron & Huebsch PLLC

(57) ABSTRACT

Systems and processes for recovering alkylene oxide, including an alkylene oxide recovery column including a stripping section located in the column to convert a portion of a feed stream to a gas phase including alkylene oxide; a reabsorption section in the column above the stripping section including a water stream to reabsorb the alkylene oxide in the gas phase portion and to produce an aqueous solution, a first stripping gas to strip carbon dioxide and oxygen from the aqueous solution by converting a portion of the aqueous solution to a gaseous portion, producing an alkylene oxide stream, and a side take-off located at a bottom portion of the reabsorption section for removal of the alkylene oxide stream; a condenser to partially condense the gas phase portion; and a top take-off for removal of a light impurity fraction.

20 Claims, 2 Drawing Sheets

FOREIGN PATENT DOCUMENTS

| | | |
|---|---|---|
| GB | 589547 | 6/1947 |
| JP | 54-16416 | 2/1979 |
| JP | 5416416 | 2/1979 |
| JP | 62-12770 | 1/1987 |
| JP | 6212770 | 1/1987 |
| WO | WO 03/055869 | 7/2003 |
| WO | WO 2004/056453 | 7/2004 |
| WO | WO 2004/056453 A1 | 7/2004 |
| WO | WO 2006/120207 | 11/2006 |
| WO | WO 2009/094103 | 7/2009 |
| WO | WO 2009/105252 | 8/2009 |

OTHER PUBLICATIONS

Viera, G.A., et al. "Lessons Learned from the Ethylene Oxide Explosion at Seadrift, Texas". Chem Eng. Progess. 89 (8), pp. 66-75 (1993).

Wankat, P.C. et al. "Two-Feed Distillation: Same-Composition Feeds with Different Enthalpies" Ind. Eng. Chem. Res. 1993, 32, 3061-3067.

Cleveland et al. "Meteor Revolution" Hydrocarbon Engineering Oct. 2001 pp. 69-71.

Xiangyu, Z. "A Comparison of EO/EG Process Technologies" Sinopec Shanghai Engineering Co. Shanghai, 2006.

ALKYLENE OXIDE RECOVERY SYSTEMS

This application claims priority to U.S. Provisional Application 61/137,493 filed Jul. 31, 2008, the specification of which is incorporated herein by reference, and is co-filed with co-owned U.S. patent applications: Ser. No. 61/137,494, Jul. 31, 2008 entitled "Alkylene Oxide Recovery Systems" filed on even date herewith, having; Ser. No. 61/137,517, Jul. 31, 2008 entitled "Alkylene Oxide Recovery Systems" filed on even date herewith, having; Ser. No. 61/137,514, Jul. 31, 2008 entitled "Alkylene Oxide Purification Processes and Systems" filed on even date herewith, having; and Ser. No. 61/137,485, Jul. 31, 2008 entitled "Alkylene Oxide Purification Systems" filed on even date herewith, having.

FIELD OF THE DISCLOSURE

This disclosure relates to a process and system for recovering alkylene oxide from feed streams containing the same. More particularly, this disclosure relates to an improved process and system for recovering alkylene oxide from a feed stream by stripping and reabsorbing alkylene oxide in a single alkylene oxide recovery column.

BACKGROUND

When ethylene oxide is prepared by a silver catalyzed, vapor phase, partial oxidation of ethylene with molecular oxygen, a gaseous reaction effluent is obtained. This effluent can be extremely dilute with respect to the desired ethylene oxide product, containing, for example, from about 0.3 mole percent to about 5 mole percent of the desired material.

Recovery of the ethylene oxide from the gaseous reaction effluent can involve an initial water absorption step, followed by a stripping step, which is in turn followed by a reabsorption step. In some instances, each of the steps is carried out in separate distillation columns, which can lead to high equipment costs and safety concerns where areas of concentrated vapor phase or liquid phase ethylene oxide exist. One exemplary area where concentrated liquid phase ethylene oxide can exist is when vapor phase ethylene oxide coming out of the top of an ethylene oxide stripper is condensed, giving liquid ethylene oxide. The liquid ethylene oxide produced in the stripper can be transported to another piece of equipment to be further refined. However, handling and/or transporting concentrated ethylene oxide, for example, liquid ethylene oxide, can be dangerous due to the risk of contamination since contaminated liquid ethylene oxide can lead to a runaway polymerization which generates heat and can be explosively violent. As such, avoiding and/or alleviating the areas of concentrated and/or contaminated liquid ethylene oxide can increase safety in the recovery of ethylene oxide.

SUMMARY

Embodiments of the present disclosure provide processes and systems for recovering alkylene oxide from a feed stream. Embodiments are adaptable to commercial scale alkylene oxide production.

In some embodiments, a system for recovery of alkylene oxide includes a stripping section located in an alkylene oxide recovery column to convert a portion of a feed stream to a gas phase portion, where the gas phase portion includes alkylene oxide. The system also includes a condenser to partially condense the gas phase portion to produce an alkylene oxide rich vapor stream and a liquid reflux stream. Additionally, the system includes a reabsorption section located in the alkylene oxide recovery column above the stripping section that includes a water stream to reabsorb the alkylene oxide in the alkylene oxide rich vapor stream to produce an aqueous solution, a stripping gas to strip carbon dioxide and oxygen from the aqueous solution by converting a portion of the aqueous solution to a gaseous portion, producing an alkylene oxide stream and a gaseous portion of the aqueous solution including carbon dioxide and oxygen, and a side take-off located at a bottom portion of the reabsorption section for removal of the alkylene oxide stream, where the alkylene oxide recovery column includes a top take-off located at a top of the column for removal of a light impurity fraction produced from stripping carbon dioxide and oxygen from the aqueous solution.

In various embodiments, a process for recovering alkylene oxide includes introducing a feed stream containing alkylene oxide to a stripping section of an alkylene oxide recovery column, where the column includes the stripping section and a reabsorption section, stripping alkylene oxide from the feed stream to form a gas phase portion in the stripping section, where the gas phase portion flows from the stripping section to the reabsorption section, and partially condensing the gas phase portion of the feed stream into a liquid reflux stream and an alkylene oxide rich vapor stream, where the liquid reflux stream is in physical communication with the stripping section. The process also includes reabsorbing the alkylene oxide in the alkylene oxide rich vapor stream into a water stream in the reabsorption section to produce an aqueous solution, stripping carbon dioxide and oxygen from the aqueous solution by converting a portion of the aqueous solution to a gaseous portion, producing an alkylene oxide stream and a gaseous portion of the aqueous solution including carbon dioxide and oxygen, and removing the alkylene oxide stream from the column at a bottom portion of the reabsorption section.

DEFINITIONS

As used herein an "alkylene oxide recovery column," or "column," refers to, for example, a generally upright, cylindrical column or tower containing separation stages that provide a surface area for a liquid and a gas to come into contact, facilitating mass transfer between the liquid and the gas. As will be appreciated, the column can also have other shapes and general orientations including a polygonal shaped column that is positioned in a horizontal orientation. The alkylene oxide recovery column includes a stripping section and a reabsorption section.

As used herein, the "stripping section" is the section of the column where one or more components of an aqueous stream, or feed stream, are removed by being placed in contact with a gas stream that is insoluble in the aqueous stream or by heating the aqueous stream to cause a phase change in the one or more components to be removed. In embodiments discussed herein, stripping can be performed on the aqueous stream to purify, recover, and/or separate alkylene oxide, where the "aqueous stream" is defined as a mixture of alkylene oxide, water, and other compounds, in liquid form.

As used herein, the "reabsorption portion" is the section of the column where components of a gas are removed by contacting the gas with a nonvolatile liquid solvent that absorbs some components of the gas while not absorbing others. Reabsorption can be employed to remove trace components from gas streams.

As used herein, a "condenser" is a device that converts vapor into liquid. In embodiments discussed herein, a gaseous portion of an aqueous solution can enter the condenser, where some compounds in the gaseous portion of the aqueous solution condense into liquid while other compounds pass through the condenser and remain in the gas phase. Also, as used herein, a "reflux condenser" is a condenser such that vapor over a boiling liquid condenses and can flow back into the vessel containing the boiling liquid to prevent the vessel's contents from boiling dry.

As used herein a "separation stage" is defined as a volume, device or combination of devices in an alkylene oxide recovery column, or a column within or at which phases are brought into intimate contact, where mass transfer occurs between the phases tending to bring them to equilibrium, and where the phases can then mechanically separated. For the various embodiments, each tray of a tray tower and/or packing of a packed tower having a height equivalent to a theoretical plate ("HETP") is a separation stage, as these are the locations where fluids are brought into intimate contact, interphase diffusion occurs, and the fluids are separated. As such, the number of trays in the column can also be attributed to an equivalent number of separation stages that are obtained by using packing. For the various embodiments, the terms separation stage, tray and/or packing having a HETP can be used interchangeably, unless otherwise stated to the contrary.

As appreciated by one skill in the art, determining a number of equilibrium stages (theoretical trays) for use in a column can be calculated based on the material balances and equilibrium considerations of the compounds to be separated in the substance. The efficiency of the separation stage, and therefore the number of separation stages that are actually used, can be determined by the mechanical design used and the condition of operation for the column. For the various embodiments provided herein, the number of equilibrium stages (or theoretical trays) could be used in place of the number of separation stages provided in the present disclosure through the use of the efficiency of the separation stage of the column.

As used herein, references to separation stage numbers are from the bottom of the column to the top of the column. So, a first separation stage is at or near the bottom of the column with subsequent separation stages being numbered progressively up the column (e.g., the second separation stage follows the first separation stage, the third separation stage follows the second, etc.).

As used herein, "a," "an," "the," "at least one," and "one or more" are used interchangeably. The terms "comprises" and variations thereof do not have a limiting meaning where these terms appear in the description and claims. Thus, for example, a stripping section located in an alkylene oxide recovery column to convert a portion of "a" feed stream to a gas phase portion can be interpreted to mean that the alkylene oxide recovery column includes "one or more" feed streams.

The term "and/or" means one, more than one, or all of the listed elements.

As used herein, the term "about" may not be limited to the precise value specified. In at least one instance, the variance indicated by the term "about" can be determined with reference to the precision of the measuring instrumentation.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION

Figure 1:
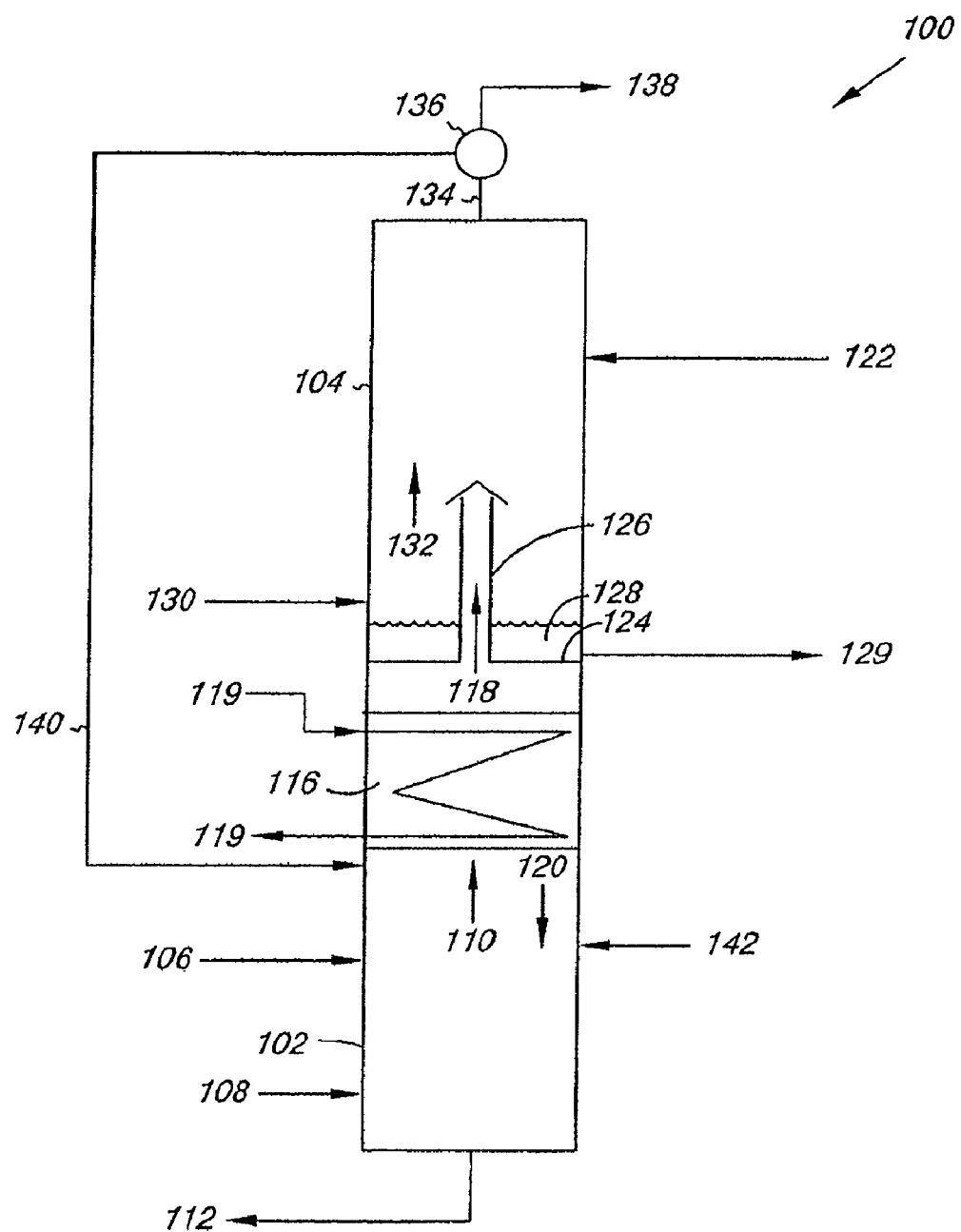
FIG. 1 provides an embodiment of a system of the present disclosure.

Embodiments of the present disclosure include processes and systems for recovering alkylene oxide from a feed stream. The system embodiments include an alkylene oxide recovery column including a stripping section, a reabsorption section above the stripping section, and a condenser.

Embodiments of the present disclosure recover alkylene oxide from a feed stream in a single column. The process includes stripping the feed stream in the stripping section of the column to produce a gas phase portion, partially condensing the gas phase portion to produce a liquid reflux stream and an alkylene oxide rich vapor stream, reabsorbing alkylene oxide in the alkylene oxide rich vapor stream to produce an aqueous solution, stripping the aqueous solution to produce an alkylene oxide stream, and removing the alkylene oxide stream from the column for further purification and/or reaction. In some embodiments, the alkylene oxide recovery column can include a condenser integral with the column at the top portion of the stripping section. As used herein, a condenser "integral" with the column refers to a condenser that is positioned inside the external walls of the column. In some embodiments, the condenser can be external to the column with appropriate connections to the column for exchange of materials to and from the condenser.

The use of a single column to perform both the stripping and reabsorption can, in some embodiments, result in lower equipment cost when building an alkylene oxide processing plant as described herein, as compared to systems having at least one stripping column and at least one reabsorption column for recovering alkylene oxide. Capital savings are achieved by combining two or more columns into a single column, resulting in a significant reduction in bulks including minimization of instrumentation, controls, pumps, piping, and plot space.

As discussed herein, embodiments of the present disclosure include recovering alkylene oxide from a feed stream. Preferred embodiments include recovering ethylene oxide from the feed stream. As such, embodiments of the present disclosure as they relate to ethylene oxide will be described herein. However, one of skill in the art will appreciate that embodiments of the present disclosure also apply to other alkylene oxides including propylene oxide, butylene oxide, methylene oxide, among others.

Also, the use of a single column can reduce safety concerns by reducing areas of concentrated vapor phase and/or liquid phase ethylene oxide. For example, by stripping and reabsorbing in a single column rather than more than one column, the ethylene oxide rich vapor stream can pass from the condenser to the reabsorption section rather than transporting the ethylene oxide rich vapor stream to a separate column for further processing. By reducing the transportation of pure or concentrated ethylene oxide, a difficult material to handle in terms of its flammability and volatility, the overall safety of the ethylene oxide process can be increased.

Before ethylene oxide can be recovered in the ethylene oxide recovery column, several steps can be performed to obtain the aqueous stream that is used as the feed stream. As described herein, the steps to produce ethylene oxide and to use ethylene oxide in further reactions can occur in one place, for example, in an ethylene oxide processing plant. The various steps, however, can also occur in separate facilities.

In addition, in an ethylene oxide production unit, the ethylene oxide production processes can be interlinked with ethylene oxide recovery processes. In certain cases where the ethylene oxide production unit is operated along with downstream product manufacturing units such as, for example an ethylene glycol manufacturing unit, the ethylene oxide processes can also be interlinked with ethylene glycol manufacturing processes to maximize energy utilization, which in turn can lower production costs.

Alkylenes (olefins) employed in the process of this disclosure can be characterized by the following structural formula (I):

wherein $R_1$ and $R_2$ are each individually selected from hydrogen and lower monovalent radicals, preferably $C_1$-$C_6$ alkyl radicals including methyl, ethyl, propyl, butyl, and higher homologues having up to six carbon atoms. Preferably, $R_1$ and $R_2$ are each individually selected from hydrogen, methyl, and ethyl. More preferably, each $R_1$ and $R_2$ is hydrogen, and the preferred olefin is ethylene. The corresponding alkylene oxides produced in the process of this disclosure are preferably characterized by the following structural formula (II):

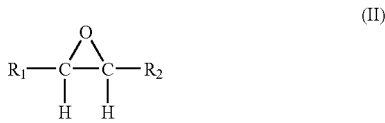

wherein $R_1$ and $R_2$ are identified herein in connection with the reactant olefin. Most preferably, the alkylene oxide is ethylene oxide (i.e., $R_1$ and $R_2$ are both hydrogen).

Oxygen may be provided to the process as pure molecular oxygen. Alternatively, oxygen may be provided as an oxygen-containing gas, where the gas further contains one or more gaseous components, for example, gaseous diluents such as nitrogen, helium, methane, and argon, which are essentially inert with respect to the oxidation process. In some embodiments, a suitable oxygen-containing gas is air. Additionally, the oxygen-containing gas may contain one or more of the following gaseous components: water, carbon dioxide, and various gaseous promoters and/or gaseous by-product inhibitors, as discussed herein.

The relative volumetric ratio of alkylene to oxygen in the feed stock gas may range in accordance with known values. Typically, the volumetric ratio of alkylene to oxygen in the feed stock may vary from about 2:1 to about 6:1. Likewise, the quantity of inert gases, diluents, or other gaseous components such as water, carbon dioxide, and gaseous promoters and gaseous by-product inhibitors, may vary in accordance with known ranges as found in the art.

The present disclosure is applicable to epoxidation reactions in a suitable reactor, for example, fixed bed reactors, fixed bed tubular reactors, continuous stirred tank reactors (CSTRs), and fluid bed reactors, a wide variety of which are known in the art. The desirability of recycling unreacted feed, employing a single-pass system, or using successive reactions to increase ethylene conversion by employing reactors in a series arrangement can also be readily determined by those skilled in the art.

The particular mode of operations selected can be dictated by process economics. Conversion of alkylene (olefin), preferably ethylene, to alkylene oxide, preferably ethylene oxide, can be carried out, for example, by continuously introducing a feed stream containing alkylene (e.g., ethylene) and oxygen, or an oxygen-containing gas, to a catalyst-containing reactor at a temperature of from about two hundred (200) degrees Celsius (° C.) to about three hundred (300) ° C., and a pressure which may be in a range of from about five (5) atmospheres (five hundred six (506) kilopascals (kPa)) to about thirty atmospheres (3040 kPa) depending on the mass velocity and productivity desired. Residence times in large scale reactors can be on the order of about 0.1 to about five (5) seconds. The resulting alkylene oxide, preferably ethylene oxide, can then be separated and recovered from the reaction products using further processes.

The alkylene oxide produced according to the present disclosure may be converted into alkylene glycols, alkanolamines, and glycol ethers. Ethylene glycol can be used in two applications: as a raw material for poly(ethylene terephthalate) for use in polyester fiber, film, and containers, and as an automotive antifreeze. Also, di-, tri-, and tetraethylene glycols are coproducts of ethylene glycol.

Ethylene glycol can be produced by the (catalyzed or uncatalyzed) hydrolysis of ethylene oxide. Ethylene oxide hydrolysis can proceed with either acid or base catalysis or uncatalyzed in neutral medium. Acid catalyzed hydrolysis activates the ethylene oxide by protonation for the reaction with water. Base catalyzed hydrolysis, however, results in considerably lower selectivity to ethylene glycol. Producing diethylene glycol and higher glycols (e.g., triethylene and tetraethylene glycols) in addition to the ethylene glycol. Ethylene glycol monoethers can be manufactured by the reaction of an alcohol with ethylene oxide. Also, ethanolamine can be manufactured by the reaction of ethylene oxide with ammonia. See, for example, U.S. Pat. No. 4,845,296.

In some embodiments, the per-pass conversion of ethylene to ethylene oxide can be low (i.e., on the order of one (1) percent or less). The gaseous reaction effluent thus formed contains dilute concentrations of ethylene oxide along with unreacted ethylene and oxygen, aldehydes, acidic impurities, nitrogen, and argon, among other components. In some embodiments, the aldehydes can include formaldehyde and acetaldehyde. In some embodiments, the per-pass conversion of ethylene to ethylene oxide can range from five (5) percent to twenty-five (25) percent.

The ethylene oxide can be separated and recovered from the gaseous reaction effluent. For example, the gaseous reaction effluent from the reactor can be scrubbed with an absorbent, such as water, to form an aqueous mixture containing ethylene oxide in an absorber column. The absorption of ethylene oxide in water can recover ethylene oxide from unreacted ethylene, oxygen, and/or other gaseous components (e.g., carbon dioxide, nitrogen, argon). The remaining gaseous materials can then be recycled as cycle gas to be mixed with the feedstock of ethylene and oxygen and fed to the ethylene oxide reactor for the production of ethylene oxide as gaseous reaction effluent.

The aqueous mixture containing ethylene oxide from the absorber column can then be passed to the ethylene oxide recovery column of the present disclosure, where the aqueous mixture, or as used herein, the feed stream, is used to produce an ethylene oxide stream with a higher ethylene oxide weight percent. The ethylene oxide stream can be removed from the column and passed to other equipment in the ethylene oxide processing plant for further purification or for use in other reactions. For example, in some embodiments, the ethylene oxide stream can be routed to a glycol unit reactor, where ethylene oxide is converted to ethylene glycol by reaction with water. The ethylene glycol produced can be monoethylene glycol, diethylene glycol, and/or triethylene glycol.

In the Figures herein, as will be appreciated, elements shown in the embodiment herein can be added, exchanged, and/or eliminated so as to provide any number of additional embodiments. In addition, as will be appreciated the proportion and the relative scale of the elements provided in the figures are intended to illustrate the embodiments of the present invention, and should not be taken in a limiting sense. The Figures herein follow a numbering convention in which the first digit or digits correspond to the drawing Figure number and the remaining digits identify an element or component in the drawing. Similar elements or components between different figures may be identified by the use of similar digits. For example, 110 may reference element "10" in FIG. 1, and a similar element may be referenced as 210 in FIG. 2. In addition, the description herein of an element and/or component provided for one or more Figures is applicable to and associated with other Figures illustrating the same element and/or component number but which do not necessarily provide the express description thereof. So, for example, when element "10" in FIG. 1 is expressly discussed herein this express discussion is also applicable to element "10" in the other Figs. where it may appear.

FIG. 1 provides a schematic representation of an embodiment of an alkylene oxide recovery column 100, or ethylene oxide recovery column 100, according to the present disclosure. As shown in the embodiment of FIG. 1, the column 100 can include a stripping section 102 and a reabsorption section 104 located in the column 100, where the reabsorption section 104 is located above the stripping section 102. In some embodiments, the stripping section 102 can be located in a lower half of the column 100 and the reabsorption section 104 can be located in an upper half of the column 100. As discussed herein, embodiments of the present disclosure can be used to recover ethylene oxide from a feed stream 106 produced from scrubbing the dilute ethylene oxide in an absorber with water.

The ethylene oxide recovery column 100, or column 100, as discussed herein, can have a diameter ranging from, for example, sixty-five (65) centimeters (cm) to six (6) meters (m) and have a height ranging from, for example, six (6) to sixty (60) m or more. For example, for the various embodiments the diameter of the column 100 can be as large as 8 m, among other diameters.

The operating conditions within the column 100 can be adjusted according to processing conditions. For example, the column 100 may be operated at a wide range of pressures, ranging from sub-atmospheric (i.e., vacuum), to near atmospheric, to super atmospheric. In practice, the general operating pressure of the column 100 can be selected during system design, although there is some flexibility to adjust the pressure of the column during normal operation. The design operating pressure of the column 100 can range from about 60 kilopascal (kPa) to about 2,200 kPa, preferably from about 80 kPa to about 1,100 kPa, and more preferably from about 100 kPa to about 450 kPa.

In addition, there can be a gradient in pressure across the column 100, with the highest pressure in the stripping section 102 and the lowest pressure in the reabsorption section 104. This gradient may be a gradual change across the column 100 and/or various sections of the column 100, or may be an abrupt pressure change. As one skilled in the art will appreciate, the pressure drop can be primarily generated across the separation stages (e.g., trays and/or packing) in the stripping section 102, as discussed further herein, across the mid-column condenser, as discussed herein, and/or across the separation stages in the reabsorption section, as discussed further herein. In addition, the pressure drop can be influenced by design and operational factors, such as vapor flux, liquid flux, the number of separation stages, the choice of packing, and/or condenser design, among other factors. The pressure gradient in the column can range from about 1 kPa to about 1,000 kPa, preferably from about 3 kPa to about 500 kPa, and more preferably from about 5 kPa to about 300 kPa.

The alkylene oxide recovery column 100 may also be operated at a wide range of temperatures. In practice, the operating temperature of the column can be selected during system design, although there can be significant variation in the column temperature during operation. In addition, there can be a temperature gradient present in the column 100, with the highest temperature in the stripping section 102 and the lowest temperature in the reabsorption section 104. This gradient may be a gradual change across the column and/or various sections of the column, or may be an abrupt temperature change. The operating temperature of the stripping section 102 can range from about 40° C. to about 200° C., preferably from about 60° C. to about 160° C., and more preferably from about 80° C. to about 140° C. The operating temperature of the reabsorption section 104 can range from about 10° C. to about 120° C., preferably from about 20° C. to about 100° C., and more preferably from about 25° C. to about 80° C.

As can be appreciated by one skilled in the art, the operating temperature of the column 100, the operating pressure of the column 100, and the composition of the feed stream 106, discussed herein, can all be highly interdependent. Also, certain sections of the column 100 can be impacted by other variables, such as the reabsorption water temperature, desired reflux ratio, pressure drop, the presence of other feed inlets and/or outlets, and/or the presence of auxiliary heaters and/or coolers. In design and operation, these variables can be optimized to provide a balance between the operating cost of the stripping section 102, the operating cost of the reabsorption section 104, and the overall column 100 capital cost. For instance, the stripping section 102 can have the lowest operating costs when run at lower pressure; however, the reabsorption section 104 can have the lowest operating costs when operated at high pressure. Other factors may also impact the chosen system operating pressure, such as column cost (e.g., higher pressure columns lead to more capital cost) or heat source availability (e.g., the heat source is required to drive the stripping section 102 to a certain temperature). In addition, often the optimum economic balance is related to heat integration requirements or other integrations requirements with other parts of the plant.

In some embodiments, the stripping section 102 can be operated at a pressure in a range from about 130 kPa to about 150 kPa and a temperature in a range of from about 100° C. to about 120° C., while the reabsorption portion 104 can be operated at a pressure in a range of from about 110 kPa to about 130 kPa and a temperature in a range of from about 30° C. to about 50° C.

In some embodiments, the stripping section 102 can have a number of components, including inlets and outlets. In the illustrated embodiment, the feed inlet is provided at an upper portion of the stripping section 102 to introduce the feed stream 106 into the stripping section 102.

In some embodiments, the feed stream 106 includes water and ethylene oxide. Examples of further possible compounds in the feed stream 106 include methane, carbon dioxide, oxygen, and ethylene, among others. In some embodiments, the composition of the feed stream 106 is about 1 weight percent to about 5 weight percent alkylene oxide, 0 weight percent to about 0.03 weight percent alkane (e.g., methane), about 0 weight percent to about 0.03 weight percent carbon dioxide, about 0 weight percent to about 0.015 weight percent oxygen, about 0 weight percent to about 0.06 weight percent alkylene with the remaining portion being made up of water.

In some embodiments, the composition of the feed stream 106 can be about 3 weight percent ethylene oxide, about 0.02 weight percent methane, about 0.02 weight percent carbon dioxide, about 0.01 weight percent oxygen, about 0.04 weight percent ethylene with the remaining portion being made up of water. The feed stream 106 may further contain impurities, namely, chlorine containing organic compounds and oxygenated hydrocarbons. In certain embodiments, the feed stream 106 can be of two phases, a liquid phase and a vapor phase.

The feed stream 106 produced from absorbing the dilute ethylene oxide mixture in the absorber, as discussed herein, can be introduced to the stripping section 102 of the column 100. In some embodiments, a second stripping gas 108 can be introduced into the stripping section 102. For example, the second stripping gas 108 can be introduced at a lower portion of the stripping section 102 to contact the feed stream 106 in a countercurrent fashion with the second stripping gas 108. In some embodiments, the second stripping gas can be steam or hot water. Steam stripping can be an economic method of separating ethylene oxide from the feed stream 106.

In some embodiments, steam can be generated within the stripping section 102 by making use of a heating mechanism placed internally or externally to the column 100. For example, a steam heated reboiler can be employed to heat water in the bottom of the stripping section 102 and boil it.

In some embodiments, the second stripping gas 108 can remove ethylene oxide by converting a portion 110 of the feed stream 106 to a gas phase portion. As used herein, the "gas phase portion" 110 is the portion of the feed stream 106 that undergoes a phase change and subsequently enters a condenser, as discussed herein.

While a portion 110 of the feed stream 106 is converted to a gas phase, the remaining portion 112 of the feed stream 106 including water, ethylene oxide, and other compounds can be removed from the bottom portion of the stripping section 102 and routed back to the absorber, as discussed herein, to collect more ethylene oxide to be brought back to the column 100 in the feed stream 106. In some embodiments, the ethylene oxide in the remaining portion 112 routed to the absorber can be in a range from zero to one thousand (1,000) mole parts per million (ppm) ethylene oxide.

The stripping section 102 can further include at least one inlet to introduce at least one input stream containing alkylene and/or alkylene oxide from an alkylene oxide pre-recovery or post-recovery process to maximize the efficiency as well as the economics of alkylene oxide production and recovery. As discussed herein, the column 100 can be part of an alkylene oxide-glycol manufacturing unit including alkylene oxide (e.g., ethylene oxide) production, concentration, purification, and optionally, glycol formation.

The stripping section 102 of the column 100 can separate ethylene oxide and other compounds from water in the feed stream 106 using vapor-liquid equilibrium stages.

As will be appreciated by one skilled in the art, the design and operation of the column 100 can depend on the composition of the feed stream 106 as well as the composition of the desired products, among other things. In some instances, for example, with a binary component feed, analytical methods such as the McCabe Thiele method or the Fenske equation can be used to determine the number of equilibrium stages to use to achieve the desired separation. For a multi-component feed stream, simulation models can be used for both design (e.g., to determine the number of equilibrium stages needed in order to achieve the desired separation) and operation (e.g., to determine the optimum operating conditions). In addition, once the number of equilibrium stages is determined, one skilled in the art can use routine experimentation to determine the number of separation stages (e.g., the actual number of trays or height of packing) to use in a column to achieve the desired separation.

The column 100 of the present disclosure can be operated with distillation trays (plates), packing, or a combination of distillation trays and packing. The distillation trays can be of the type of plates commonly found in distillation columns, such as sieve plates, bubble-cap plates or valve plates, among others. In some embodiments, the distance between each tray can vary. In addition, in embodiments using packing, the packing material can be random dumped packing such as, for example, Raschig rings, Pall rings, or Bialecki rings in metal or ceramic. The packing material can also be structured sheet-metal packing such as those known and commercially available for example under the designations Gempak® (Kock-Glitsch, LP, Dallas, Tex., U.S.A) and/or Mellapak® (Gebr. Sulzer, Winterthur, Switzerland).

In embodiments where random packing is employed, the total required height of packing to provide the required number of separation stages can be determined by multiplying the number of calculated equilibrium stages by the Height Equivalent to a Theoretical Plate, or HETP. The HETP is a value of the height of packing that will give the same separation as an equilibrium stage. As known to one skilled in the art, the HETP can vary depending on the type of packing selected.

In some embodiments, the total height of packing can be split into one or more zones with vapor-liquid redistributors in between the zones, for example, to accommodate height limitations due to packing structural integrity or to accommodate feed streams or product streams. In some embodiments, packing may offer the advantage of a lower pressure drop as compared to trays, although consideration must also be given to the cost difference arising from the choice of trays versus packing.

The stripping section 102 of the column 100 of the present disclosure can be operated in such a way as to include between 4 and 14 separation stages, preferably between 6 and 12 separation stages, and more preferably between 7 and 11 separation stages. As such, when the stripping section 102 is configured as a tray tower it can include trays in a range of about 6 to about 25. In some embodiments, the distance between each tray can vary, where the distance between each tray is optimized for the best separation of the feed stream 106 components at the specific temperature and pressure of each tray.

In some embodiments, each tray can be at a different temperature and pressure, where the stripping section 102 bottom has the highest pressure and temperature. In some embodiments, progressing upwards in the stripping section 102 includes decreasing temperature and pressure for each succeeding stage. In some instances, the vapor-liquid equilibrium for each feed component of the feed stream 106 in the stripping section 102 reacts in a unique way to the different pressure and temperature conditions at each of the separation stages. That means, in some embodiments, each component establishes a different concentration in the vapor and liquid phases at each of the separation stages, resulting in the separation of components in the feed stream 106.

As discussed herein, calculating the number of equilibrium stages needed in order to achieve a desired separation can be determined using the McCabe Thiele method, the Fenske equation, or simulation models. As one skilled in the art will appreciate, once the number of equilibrium stages in the stripping section 102 is calculated using the methods mentioned, the range of actual trays (separation stages) can be determined using routine experimentation.

As discussed herein, the stripping section 102 can convert a portion 110 of the feed stream 106 to a gas phase portion, where the gas phase portion 110 of the feed stream 106 includes ethylene oxide. In some embodiments, the gas phase portion 110 of the feed stream 106 can also include carbon dioxide, oxygen, and/or aldehydes, for example, formaldehyde and acetaldehyde. In addition, the gas phase portion 110 can include water and other components from the second stripping gas 108, as discussed herein.

As shown in FIG. 1, the gas phase portion 110 can flow from the stripping section 102 to a condenser 116 to cool and partially condense the gas phase portion 110, producing an ethylene oxide rich vapor stream 118 and a liquid reflux stream 120. In some embodiments, the condenser can include, for example, a cooling water stream 119 flowing countercurrent with the flow of the gas phase portion 110 to cool and partially condense the gas phase portion 110.

As illustrated in FIG. 1, in some embodiments, the condenser 116 can be located at a top portion of the stripping section 102 integral with the column 100. In such embodiments, the condenser 116 can be a reflux condenser. A reflux condenser can return condensed vapors (e.g., the liquid reflux stream 120) directly to the stripping section 102, and any noncondensable gases (e.g., the ethylene oxide rich vapor stream 118) can be released at the top of the condenser 116. In some embodiments, a portion of the heat removed from the condenser 116 may be usefully employed in other parts of the ethylene oxide recovery column process and/or in other parts of the ethylene oxide processing plant.

In some embodiments, the gas phase portion 110 can enter the condenser 116 at a temperature in a range of about ninety (90) to one hundred (100) ° C. In addition, in some embodiments, the ethylene oxide rich vapor stream 118 exiting the condenser 116 can be at a temperature in a range of about thirty-five (35) to forty-five (45) ° C. Also, when the ethylene oxide rich vapor stream 118 is in the temperature range of about thirty-five (35) to about forty-five (45) ° C., the ethylene oxide rich vapor stream 118 can include about eighty-seven (87) to about ninety-one (91) mole percent ethylene oxide and about four (4) to about seven (7) mole percent water, among other compounds.

As illustrated in FIG. 1, the ethylene oxide rich vapor stream 118 can be introduced to the reabsorption section 104 of the column 100. In some embodiments, the reabsorption section 104 can absorb ethylene oxide in the ethylene oxide rich vapor stream 118 by contacting the ethylene oxide rich vapor stream 118 with a water stream 122 to absorb the ethylene oxide content thereof.

In some embodiments, the reabsorption section 104 absorbs ethylene oxide using vapor-liquid separation stages, as discussed herein. The reabsorption section 104 of the column 100 of the present disclosure can have trays, dumped packing, structured packing, or a mixture of trays and packing, as discussed herein. In some embodiments, the reabsorption section 104 can be operated in such a way as to include between 2 and 10 separation stages, preferably between 3 and 9 separation stages, and more preferably between 4 and 8 separation stages. In addition, in some embodiments, when the reabsorption section 104 is configured as a tray tower it can include trays in a range of about four (4) to eighteen (18) trays positioned in the reabsorption section 104 with a uniform distance between each tray.

In some embodiments, the reabsorption section 104 can use packing rather than trays, where the total packing height required can be determined by multiplying the number of theoretical stages (e.g., seven) by the HETP, as discussed herein. In some embodiments, the reabsorption section 104 can include a mixture of packing and trays. Similar to the stripping section 102, the equilibrium stages can be calculated using the McCabe Thiele method, the Fenske equation, or simulation models. As one skilled in the art will appreciate, once the number of equilibrium stages in the reabsorption section 104 is determined using the methods mentioned, the range of actual trays can be determined using routine experimentation.

In some embodiments, the reabsorption section 104 can include a chimney tray 124 located at the bottom portion of the reabsorption section 104. As used herein, a "chimney tray" is a tray designed in such a way that it will allow vapor to rise through it, but it can prevent liquid from passing down through it by accumulating the down flowing liquid over a collection tray. Thus, a chimney tray 124 can be used when the objective is to let vapor pass through a tray and collect the liquid coming down to the tray. In some embodiments, the chimney tray 124 can be a solid tray of metal with a chimney 126, or standpipe, topped by a hat to keep liquid from raining down through the standpipe. A "hat," as used herein, refers to a cover that is loosely connected to the standpipe to allow vapor to flow up and out of the standpipe, while preventing liquid from entering the standpipe from the reabsorption section 104. A "standpipe," or chimney, as used herein, is an open pipe which extends through the tray and some distance above the tray so that liquid can stand and accumulate on the tray.

As will be appreciated, the chimney tray 124 may additionally enhance distribution of an up-flowing vapor through the column 100, where the column may contain trays, dumped packing, structured packing, or a mixture of trays and packing. In addition, the chimney tray 124 can be designed to overflow the collected liquid back into the stripping section 102 via the chimney 126 during upset conditions. As used herein, the term "upset conditions" is defined as the conditions in which there is a disturbance and/or deviation from normal functioning of the process.

In some embodiments, the ethylene oxide rich vapor stream 118 can enter the reabsorption section 104 by passing through the chimney 126. In addition, in some embodiments where the reabsorption section 104 includes either packing or a mixture of trays and packing, the chimney 126 can be designed such that the top of the chimney 126 extends past some of the packing in the reabsorption section 104 of the column 100.

As discussed herein, the reabsorption section 104 can include a water stream 122 to contact with the ethylene oxide rich vapor stream 118, reabsorbing the ethylene oxide in the ethylene oxide rich vapor stream 118 to produce an aqueous solution 128. In some embodiments, the aqueous solution 128 can collect on the chimney tray 124.

The reabsorption section 104 can also include a first stripping gas 130 introduced into the reabsorption section 104 to strip carbon dioxide and oxygen from the aqueous solution 128. In some embodiments, the first stripping gas can be steam or hot water and can be contacted with the aqueous solution 128 to convert a portion of the aqueous solution 128 to a gaseous portion, producing an ethylene oxide stream 129 and a gaseous portion of the aqueous solution 132 including carbon dioxide and oxygen. The gaseous portion of the aqueous solution 132 is taken out of the reabsorption section 104 via a top take-off located at a top of the column 100 as a light impurity fraction 134.

In some embodiments, a reboiler can be employed to heat the aqueous solution 128 in the bottom of the reabsorption section 104 and boil it. This can generate the first stripping gas internally in the reabsorption section 104. The reboiler can be heated with steam or other suitable condensable vapor stream or a hot liquid such as hot water As discussed herein, in the reabsorption section 104 a water stream 122 can enter the column 100 to reabsorb ethylene oxide in the ethylene oxide rich vapor stream 118 while the first stripping gas 130 can enter the column 100 to strip carbon dioxide and oxygen from the aqueous solution 128. As will be appreciated by one skilled in the art, the flow rate, composition, and temperature of the water stream 122 can affect the amount of ethylene oxide exiting the top of the column 100 in the light impurity fraction 134 and the amount of ethylene oxide in the ethylene oxide stream 129 exiting the column 100 at the bottom of the reabsorption section 104. The water stream 122 can also contain low levels of other materials, such as dissolved gases, alkylene glycols, and part-per-million levels of aldehydes. For example, the water stream 122 can include at least about 90 weight percent water, preferably at least about 92 weight percent water, and most preferably at least about 95 weight percent water, based on the total weight of the water stream 122. In addition, although water is a preferred absorbing medium for the alkylene oxide recovery column 100, other absorbing mediums can also be used, including alkylene glycols, alkylene carbonates, glyme, and/or ionic liquids, among others. In some embodiments, the water stream 122 can have a temperature in a range of from about 5° C. to about 80° C., preferably from about 15° C. to about 60° C., and more preferably from about 25° C. to about 50° C.

By controlling the water stream 122 temperature and flow to the column 100, the impurity fraction 134 can include less than, for example, about one hundred (100) mole parts per million (ppm) ethylene oxide. In addition, by controlling the first stripping gas 130, the concentration of carbon dioxide in the ethylene oxide stream 129 exiting the column 100 can be controlled. In some embodiments, the carbon dioxide in the aqueous solution 128 can be in a range of about five (5) to about ten (10) mole ppm.

As illustrated in the embodiment of FIG. 1, the ethylene oxide stream 129 can be removed from the column 100 at a side take-off location located at a bottom portion of the reabsorption section 104 and routed for further purification or routed to a glycol unit reactor, as discussed herein. In some embodiments, the ethylene oxide stream 129 can include about zero (0) to about fifteen (15) weight percent ethylene oxide. As will be appreciated by one skilled in the art, the zero (0) ethylene oxide condition represents a pre-startup, standby condition, and the higher end of the range represents full rate operation. The column 100 is capable of transitioning smoothly over the entire range. In addition, the temperature of the ethylene oxide stream 129 exiting the column can vary slightly depending on process conditions (e.g., water stream 122 temperature, rate of the water stream 122 flow, the amount of gas injected in the stripping gas 130, etc.), however, the temperature of the ethylene oxide stream 129 can be about fifty (50) to about eighty (80) ° C., with the higher temperature corresponding to an ethylene oxide operation using a lower feed stream 106 flow rate as compared to the higher temperature ethylene oxide operation.

As discussed herein, in some embodiments, the ethylene oxide stream 129 can be routed to the glycol unit reactor where ethylene oxide is converted to ethylene glycol by reaction with water. In some embodiments, water, in excess in the glycol unit reactor, can be distilled away from the ethylene glycol, condensed, and sent back to the column 100 in the form of the water stream 122 to reabsorb more ethylene oxide.

In some embodiments, the column 100 includes a vent gas compressor 136 that can take suction from the column 100, where the vent gas compressor 136 compresses the light impurity fraction 134 so that it can be recycled, producing a compressed impurity fraction 138 and a condensed liquid 140. In some embodiments, the compressed impurity fraction 138 can be recycled back to the ethylene oxide reactor, as discussed herein. In some embodiments, the condensed liquid 140 can form during the compression of the light impurity fraction 134. In some embodiments, the condensed liquid 140 can be recycled back to the stripping section 102 of the column 100 to recover ethylene oxide that may be present in the condensed liquid 140.

As described herein, the column 100 of the present disclosure can serve as a receiving location for various streams containing ethylene oxide resulting from other processes occurring in an ethylene oxide processing plant. For example, in some embodiments, the ethylene oxide processing plant can include a carbon dioxide absorber. A carbon dioxide absorber can be an absorption column where carbon dioxide is taken out of a gas recycle stream. To keep from venting the ethylene oxide in the carbon dioxide vent to the atmosphere, a rich solution flash tank can be employed, where the majority of the gases from the carbon dioxide absorber rich solution are flashed off and collected. In some embodiments, the gases flashed off of the carbon dioxide absorber rich solution can be sent to the ethylene oxide recovery column 100 as a carbon dioxide regenerator flash tank overhead stream 142, or overhead stream 142.

In some embodiments, the overhead stream 142 can be fed to the stripping section 102 to remove impurities in the overhead stream 142 and to decrease the heat load on the vent gas compressor 136. By feeding the overhead stream 142 to the stripping section 102 of the column, the overhead stream 142 can cool as it passes through the condenser 116 and any impurities (e.g., salts) included in the overhead stream 142 can be washed out. By cooling the overhead stream 142 before it enters the reabsorption section 104, the heat load on the vent gas compressor 136 can be decreased.

In addition to the overhead stream 142 from the carbon dioxide absorber, other ethylene oxide containing streams can also be sent to the column 100, including an ethylene oxide purification column vent, an ethylene oxide clean-up header, and an ethylene oxide storage tank scrubber water, among others.

Figure 2:
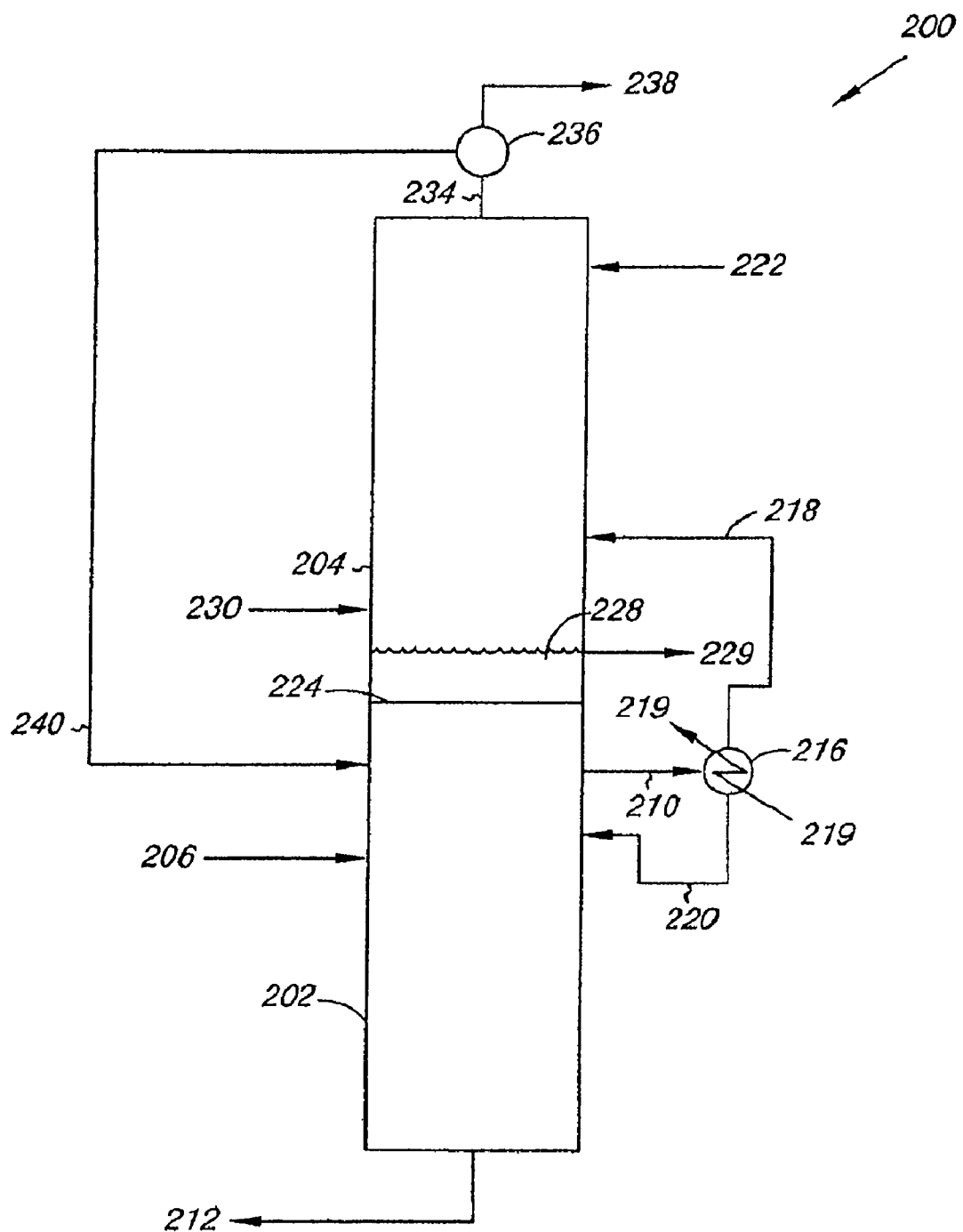
FIG. 2 provides an embodiment of a system of the present disclosure.

FIG. 2 provides an embodiment of an ethylene oxide recovery column 200 according to the present disclosure. The embodiment illustrated in FIG. 2 can be operated in substantially the same way as discussed herein with respect to FIG. 1; however, the condenser 216 is located outside the column 200, and the column includes a tray 224, but not a chimney as shown in FIG. 1. As discussed herein, the embodiment of the column 200, as shown, includes a stripping section 202 and a reabsorption section 204. Also, a feed stream 206 can be introduced into the stripping section 202 to convert a portion of the feed stream 210 to a gas phase, as discussed herein.

As shown in FIG. 2, the gas phase portion 210 can exit the stripping section 202 and the column 200 to be sent to the condenser 216 to cool and partially condense the gas phase portion 210 to produce an ethylene oxide rich vapor stream 218 and a liquid reflux stream 220. In some embodiments, the ethylene oxide rich vapor stream 218 can reenter the column 200 at the reabsorption section 204, and the liquid reflux stream 220 can be routed back into the stripping section 202.

The ethylene oxide in the ethylene oxide rich vapor stream 218 can be reabsorbed into water in the reabsorption section 204 by a water stream 222 entering a top portion of the reabsorption section 204, as discussed herein. Also, the ethylene oxide in the ethylene oxide rich vapor stream 218 reabsorbed into the water stream 222 can form an aqueous solution 228, as discussed herein. In addition, the reabsorption section 204 can include a stripping gas 230 to remove carbon dioxide and oxygen from the aqueous solution 228.

As discussed herein, the ethylene oxide rich vapor stream 218 can be fed to the reabsorption section 204. In some embodiments, the ethylene oxide rich vapor stream 218 can be fed to the reabsorption section 204 at an elevation higher than the feed point of the first stripping gas 230. In some embodiments, the ethylene oxide rich vapor stream 218 can be reabsorbed into the water stream 222, where the aqueous solution 228 formed therein can collect on the tray 224. The aqueous solution 228 can then be stripped of carbon dioxide and oxygen by introduction of the first stripping gas 230. The ethylene oxide stream 229 can then be removed from the column 200 at a side take-off located at the bottom portion of the reabsorption section 204. In some embodiments, the ethylene oxide stream 229 removed from the column 200 can be routed to a glycol reactor to convert ethylene oxide to ethylene glycol, as discussed herein. The ethylene oxide stream 229 can also be routed for further purification, or for other reactions.

For the various embodiments, the ethylene oxide provided according to the present disclosure can be processed to provide further downstream products, such as, for example, 1,2-diols, 1,2-diol ethers, 1,2-carbonates, and alkanolamines. Since the present disclosure provides improvements to the separation and purity of the ethylene oxide, it is contemplated that the improvements provided herein will carry forward to provide improvements to these downstream processes and/or products. Improved methods for the production of 1,2-diols, 1,2-carbonates, 1,2-diol ethers and alkanolamines are thus also provided herein.

The conversion of ethylene oxides into 1,2-diols or 1,2-diol ethers may comprise, for example, reacting the ethylene oxide with water, suitably in the presence of an acidic or basic catalyst. For example, for preferential production of the 1,2-diol over the 1,2-diol ether, the ethylene oxide may be reacted with a tenfold molar excess of water, in a liquid phase reaction in the presence of an acid catalyst, e.g., 0.5-1.0 wt % sulfuric acid, based on the total reaction mixture, at 50-70° C. at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternatively, 1,2-diol ethers may be prepared by converting the ethylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of ethylene oxide provided according to the present disclosure into alkanolamines may comprise, for example, reacting the ethylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

As discussed herein, the carbon dioxide and oxygen removed from the aqueous solution 228 can be removed from the top of the column 200 as a light impurity fraction 234. The impurity fraction 234 can be compressed via a vent gas compressor 236 that can take suction from the column 200, and the compressed impurity fraction 238 can be recycled to the ethylene oxide reactor, while the condensed liquid 240 can be routed back to the stripping section 202, as discussed herein.

It is to be understood that the above description has been made in an illustrative fashion, and not a restrictive one. Although specific embodiments have been illustrated and described herein, those of ordinary skill in the art will appreciate that other component arrangements can be substituted for the specific embodiments shown. The claims are intended to cover such adaptations or variations of various embodiments of the disclosure, except to the extent limited by the prior art.

In the foregoing Detailed Description, various features are grouped together in exemplary embodiments for the purpose of streamlining the disclosure. This method of disclosure is not to be interpreted as reflecting an intention that any claim requires more features than are expressly recited in the claim. Rather, as the following claims reflect, inventive subject matter lies in less than all features of a single disclosed embodiment. Thus, the following claims are hereby incorporated into the Detailed Description, with each claim standing on its own as a separate embodiment of the invention.

What is claimed:

1. A system for recovery of alkylene oxide, comprising:
   a stripping section located in an alkylene oxide recovery column to convert a portion of a feed stream to a gas phase portion, where the gas phase portion includes alkylene oxide;
   a condenser to partially condense the gas phase portion to produce an alkylene oxide rich vapor stream and a liquid reflux stream; and
   a reabsorption section located in the alkylene oxide recovery column above the stripping section including:
      a water stream to reabsorb the alkylene oxide in the alkylene oxide rich vapor stream to produce an aqueous solution;
      a first stripping gas to strip carbon dioxide and oxygen from the aqueous solution by converting a portion of the aqueous solution to a gaseous portion, producing an alkylene oxide stream and a gaseous portion of the aqueous solution including carbon dioxide and oxygen; and
      a side take-off located at a bottom portion of the reabsorption section for removal of the alkylene oxide stream, where the alkylene oxide recovery column includes a top take-off located at a top of the column for removal of a light impurity fraction produced from stripping carbon dioxide and oxygen from the aqueous solution.

2. The system of claim 1, where the stripping section includes a carbon dioxide regenerator flash tank overhead stream from a carbon dioxide absorber that is collected with the impurity fraction.

3. The system of claim 1, where the condenser is located at a top portion of the stripping section integral with the column.

4. The system of claim 1, where the column includes a mixture of trays and packing in at least one of the stripping section and the reabsorption section.

5. The system of claim 1, where the stripping section includes packing with about 8 separation stages.

6. The system of claim 5, where the reabsorption section includes packing with about 7 separation stages.

7. The system of claim 1, where the stripping section includes about 16 to 20 separation stages.

8. The system of claim 7, where the reabsorption section includes about 14 to 18 separation stages.

9. The system of claim 1, further including a chimney tray located at the bottom portion of the reabsorption section, where the aqueous solution collects on the chimney tray while the alkylene oxide rich vapor stream passes through a chimney included on the chimney tray and into the reabsorption section.

10. The system of claim 1, where the stripping section includes a second stripping gas to convert the portion of the feed stream to the gas phase.

11. A process for recovering alkylene oxide, comprising:
introducing a feed stream containing alkylene oxide to a stripping section of an alkylene oxide recovery column, where the column includes the stripping section and a reabsorption section;
stripping alkylene oxide from the feed stream to form a gas phase portion in the stripping section, where the gas phase portion flows from the stripping section to the reabsorption section;
partially condensing the gas phase portion into a liquid reflux stream and an alkylene oxide rich vapor stream, where the liquid reflux stream is in physical communication with the stripping section;
reabsorbing the alkylene oxide in the alkylene oxide rich vapor stream into a water stream in the reabsorption section to produce an aqueous solution;
stripping carbon dioxide and oxygen from the aqueous solution by converting a portion of the aqueous solution to a gaseous portion, producing an alkylene oxide stream and a gaseous portion of the aqueous solution including carbon dioxide and oxygen; and
removing the alkylene oxide stream from the column at a bottom portion of the reabsorption section.

12. The process of claim 11, further including removing a light impurity fraction as a top exit stream from the column located at a top take-off on the column.

13. The process of claim 12, further including introducing a carbon dioxide regenerator flash tank overhead stream into the stripping section from a carbon dioxide absorber, where the flash tank overhead stream is collected with the impurity fraction.

14. The process of claim 11, where partially condensing the gas phase portion includes passing the gas phase portion through a condenser.

15. The process of claim 14, where the condenser is located outside the column, and where the gas phase portion exits the stripping section to be fed to the condenser, and the alkylene oxide rich vapor stream is fed to the reabsorption section.

16. The process of claim 11, where stripping carbon dioxide and oxygen from the aqueous solution includes introducing a first stripping gas into a bottom portion of the reabsorption section to strip carbon dioxide and oxygen from the aqueous solution.

17. The process of claim 11, where stripping carbon dioxide and oxygen from the aqueous solution includes heating the aqueous solution to produce steam to strip carbon dioxide and oxygen from the aqueous solution.

18. The process of claim 11, where stripping alkylene oxide from the feed stream includes introducing a second stripping gas into a bottom portion of the stripping section of the column to strip alkylene oxide from the feed stream.

19. The process of claim 11, where stripping alkylene oxide from the feed stream includes heating the feed stream to produce steam to strip alkylene oxide from the feed stream.

20. The process of claim 11, where stripping carbon dioxide and oxygen from the aqueous solution includes introducing a methane stream into a bottom portion of the reabsorption section to strip carbon dioxide and oxygen from the aqueous solution.

* * * * *